(12) United States Patent
Jeon et al.

(10) Patent No.: US 7,947,491 B2
(45) Date of Patent: May 24, 2011

(54) MICROFLUIDIC GRADIENT DEVICES

(75) Inventors: Noo Li Jeon, Irvine, CA (US); Wajeeh Saadi, Cambridge, MA (US); Seog Woo Rhee, Kongju (KR); Bobak Mosadegh, Ann Arbor, MI (US); Carlos Huang, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 840 days.

(21) Appl. No.: 11/849,194

(22) Filed: Aug. 31, 2007

(65) Prior Publication Data
US 2011/0003372 A1    Jan. 6, 2011

Related U.S. Application Data

(60) Provisional application No. 60/841,798, filed on Aug. 31, 2006, provisional application No. 60/841,721, filed on Aug. 31, 2006.

(51) Int. Cl.
 C12M 3/00   (2006.01)
 C12M 1/34   (2006.01)
(52) U.S. Cl. .................................................. 435/288.5
(58) Field of Classification Search ............... 435/4, 7.1, 435/283.1, 287.1–287.3, 288.5–288.7
See application file for complete search history.

(56) References Cited

U.S. PATENT DOCUMENTS

| 7,141,429 | B2 * | 11/2006 | Munson et al. ................ 436/53 |
| 2004/0106129 | A1 | 6/2004 | Crook et al. |
| 2004/0121066 | A1 | 6/2004 | Anderson et al. |
| 2005/0217750 | A1 | 10/2005 | Jeon et al. |
| 2005/0266582 | A1 * | 12/2005 | Modlin et al. ................ 436/164 |
| 2007/0178582 | A1 * | 8/2007 | Koser ........................ 435/288.5 |
| 2008/0014575 | A1 * | 1/2008 | Nelson ............................. 435/5 |

OTHER PUBLICATIONS

Duffy, et al. "Rapid prototyping of microfluidic systems in poly(dimethylsiloxane)," Anal. Chem. 1998, vol. 70, No. 23; pp. 4974-4984.

\* cited by examiner

*Primary Examiner* — Walter D Griffin
*Assistant Examiner* — Shanta G Doe
(74) *Attorney, Agent, or Firm* — Seth D. Levy; Davis Wright Tremaine LLP

(57) ABSTRACT

The present invention relates to devices and systems that may generate and maintain a chemical gradient. In one embodiment, the invention provides a source and a sink channel so that a gradient bridge is created. In another embodiment, the gradient bridge creates a stable environment for facilitating molecular events to occur, such as a cell migration, or formation of crystallized molecules.

25 Claims, 8 Drawing Sheets

MICROFLUIDIC GRADIENT DEVICES

CROSS REFERENCE TO RELATED APPLICATIONS

This application claims priority to U.S. Provisional Application Ser. No. 60/841,721 filed Aug. 31, 2006, and to U.S. Provisional Application Ser. No. 60/841,798 filed Aug. 31, 2006, the disclosures of which are incorporated herein by reference.

STATEMENT REGARDING FEDERALLY SPONSORED RESEARCH

The generation of the contents of this application was supported in part by Grant Nos. DAMD17-03-10515 and DAMD17-03-1-0673 awarded by the Department of Defense (DOD). Accordingly, the government may have certain rights in invention(s) derived therefrom.

TECHNICAL FIELD

Provided herein are apparatuses, systems and methods for generating concentration gradients of soluble molecules.

BACKGROUND

In the chemical, biomedical, bioscience and pharmaceutical industries, it has become increasingly desirable to perform large numbers of chemical operations in a highly parallel fashion. The formation of microfluidic concentration gradients can facilitate such operations. Microfluidic devices and systems provide improved methods of performing chemical, biochemical and biological analysis and synthesis. Chip-based microfluidic systems have been developed. Typically, such devices include chambers and reservoirs connected by channels. Reproducible and cost-effective devices, systems and methods for forming temporal and spatial microfluidic concentration gradients in 2D and 3D environments are desirable.

SUMMARY

The present application relates, in general, to the field of devices and systems for generating and maintaining a chemical gradient. In particular, the present application relates to devices that make use of a gradient chamber or gradient bridge associated with source and sink channels to facilitate the generation of a stable gradient in an environment suitable for facilitating molecular events. In some embodiments, the devices systems and methods facilitate the identification of factors that modulate molecular events such as cell migration or the formation and isolation of crystallized molecules.

Accordingly, in one embodiment a gradient device is provided. The device includes a source channel in fluid communication with a first inlet; a sink channel in fluid communication with a second inlet and substantially parallel to the first channel; and at least one gradient chamber substantially proximal to the source channel and the sink channel. The terminal ends of the gradient are fluidly connected to the first channel and the second channel. In general, the dimensions of the gradient chamber are suitable for forming a gradient generating region substantially exclusively by diffusion.

In another embodiment, a gradient device is provided. The device includes a source channel in fluid communication with a first inlet and a sink channel in fluid communication with a second inlet and substantially parallel to the source channel. The device further includes at least one gradient bridge disposed in proximity to the source channel and sink channel, the gradient bridge optionally in fluid communication with a bridge channel and including at least a first aperture in fluid communication with the source channel and at least a second aperture in fluid communication with the sink channel. In general, the gradient bridge and the gradient channel are configured to i) facilitate the formation of a gradient generating region substantially exclusively by diffusion and ii) contain a matrix suitable for sustaining cell migration.

In another embodiment, a platform that includes a plurality of gradient devices is provided.

In yet another embodiment, a system is provided. The system includes a gradient device or platform as provided herein. The system further includes a controller operably associated with the gradient device or platform, or any combination thereof. In general, the controller is configured to control fluid movement through the channels during operation of the device or platform. The system also includes a detector assembly configured to capture a molecular event associated with a gradient generating region.

In yet another embodiment, a method of generating a gradient is provided. The method includes introducing a source constituent into the source channel of a device provided herein and introducing a sink constituent into the sink channel of a device provided herein. Further providing a constant flow of source constituent and sink constituent and generating a gradient in the gradient chamber or gradient bridge of a device provided herein. The gradient includes a substantially constant gradient profile.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

FIG. 3 panel B depicts an embodiment of a gradient device including exemplary gradient bridges suitable for generating gradients in three-dimensions;

FIG. 3 panel C depicts an exemplary gradient chamber including apertures suitable for producing a non-linear gradient;

FIG. 3 panel D depicts an exemplary gradient channel including asymmetric apertures suitable for producing a non-linear gradient;

FIG. 4 panel B depicts an exemplary gradient profile (right panel) and fluorescent images (left panel) produced by a gradient device provided herein;

FIG. 4 panel C depicts an exemplary gradient profile (right panel) and fluorescent images (left panel) produced by a gradient device provided herein;

FIG. 5 panel B depicts a phase micrograph of the gradient chambers shown in FIG. 5 panel A;

FIG. 5 panel C depicts a cross section of an embodiment of a gradient device;

FIG. 6 panel B depicts a phase micrograph of collagen gels formed in the gradient bridges shown in FIG. 6 panel A;

FIG. 6 panel C depicts a phase micrograph of collagen gels formed in the gradient bridges shown in FIG. 6 panel A;

DETAILED DESCRIPTION

Devices, systems and methods for the efficient generation of concentration gradients in two-dimensional (2D) and three dimensional (3D) environments are provided.

Figure 1:
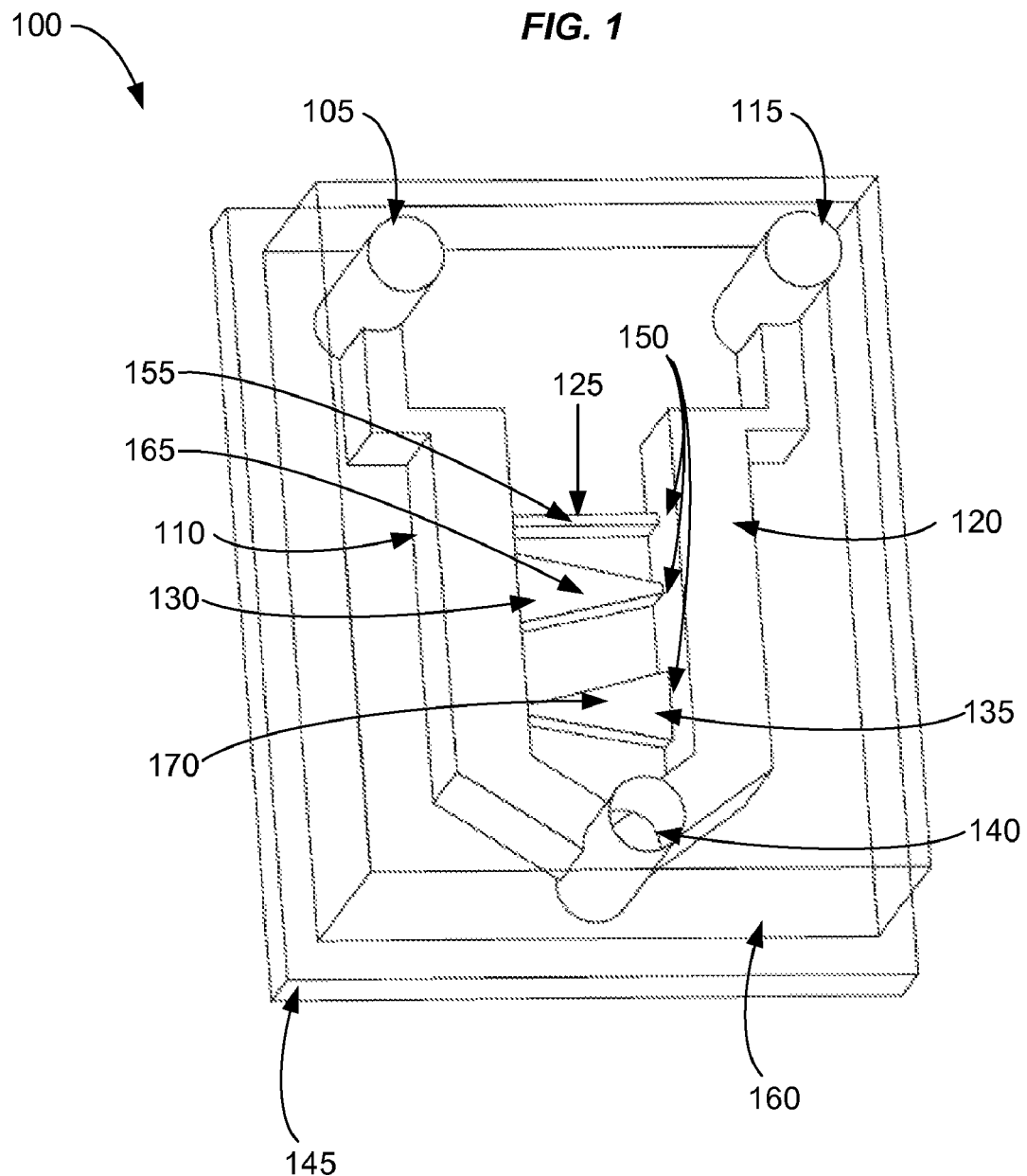
FIG. 1 depicts an embodiment of a gradient device including exemplary gradient chambers.

An exemplary embodiment of a gradient generating device is depicted in FIG. 1. Gradient device 100 includes base 145 associated with substrate 160. Substrate 160 includes sink inlet 105 which provides for the movement of materials (either by mass fluid flow or molecular diffusion) into sink channel 110, and outlet 140 which provides for movement of materials out of sink channel 110 and source channel 120. Sink channel 110 and source channel 120 may be associated with sink inlet 105 and source inlet 115, respectively. It is understood that while FIG. 1 depicts a common outlet for sink channel 110 and source channel 120, devices provided herein encompass the use of individual outlet channels associated with each channel. Source inlet 115 provides for the movement of a source constituent (either by mass fluid flow or molecular diffusion) into source channel 120. Sink inlet 105 provides for the movement of a sink constituent (either by mass fluid flow or molecular diffusion) into sink channel 110. At least one gradient chamber is located in proximity to, and in fluid communication with, sink channel 110 and source channel 120. FIG. 1 depicts multiple exemplary gradient chambers suitable for forming gradients. Symmetric gradient chamber 125 is suitable for generating a linear gradient in gradient generating region 155. Asymmetric gradient chamber 130 is suitable for generating a non-linear gradient in gradient generating region 165. Asymmetric gradient chamber 135 is suitable for generating a non-linear gradient in gradient generating region 170. Substrate 160 includes channels, chambers, inlets, outlets and other elements associated with gradient device 100 or 200 (see FIG. 2). Substrate 160 can be manufactured from any material suitable for forming microfluidic structures associated with the transport of minute quantities of substances.

The formation of a gradient in a gradient generating region 155, 165, 170 may be modulated by various modifications to the device. For example, the height of the gradient chamber 150 in relation to the source and sink channel can be modified. As the device generates gradients across a gradient generating region by free-diffusion between a source and a sink channel, convective flow through a gradient chamber may be minimized by designing the height of the gradient chamber to be substantially less than that of the main channels (e.g. the source and sink channels. The gradient chamber height to sink or source height ratio can be 1:2, 1:5, 1:10, 1:15, 1:20, 1:25, 1:30, 1:40, 1:50, 1:75, 1:100 or 1:500. In practice, a large difference in gradient chamber height yields an even larger difference in fluidic resistance causing flow to take the path of least resistance (e.g., sink or source channel) rather than entering the gradient chamber, allowing only diffusive transport.

A source constituent and sink constituent are included in source channel and sink channel, respectively. Diffusion occurs between a source constituent and a sink constituent which are in fluid communication with each other via a gradient chamber (see FIG. 1) or gradient bridge (see FIG. 2). Free-diffusion between source and sink constituents occurs through the finite volume of a gradient chamber or gradient bridge, producing a concentration gradient which can be detected and/or measured.

Based upon the biologic or chemical structure of the sink constituent, the presence or absence of the source constituent's diffusion rate toward the sink constituent, and/or the rate of that diffusion, the activity of the source constitute can be ascertained. Analogously, knowledge of the biologic or chemical makeup of the source constituent and the aforementioned presence (or absence) and source constituent's rate of diffusion, conclusions as to the activity of the sink constituent can be made. For generating crystalline structures of a target molecule, the target molecule can be included in the sink constituent in the presence of a particular buffer. The source constituent may contain a similar buffer but at a different pH and/or including a different salt concentration. The gradient will form in a gradient generating region reflecting the diffusion of the source and sink constituents, thereby facilitating formation of a crystal structure of the target molecule in the region. In this example, the detectable molecular event includes the formation of a crystalline structure of a target molecule.

Figure 3:
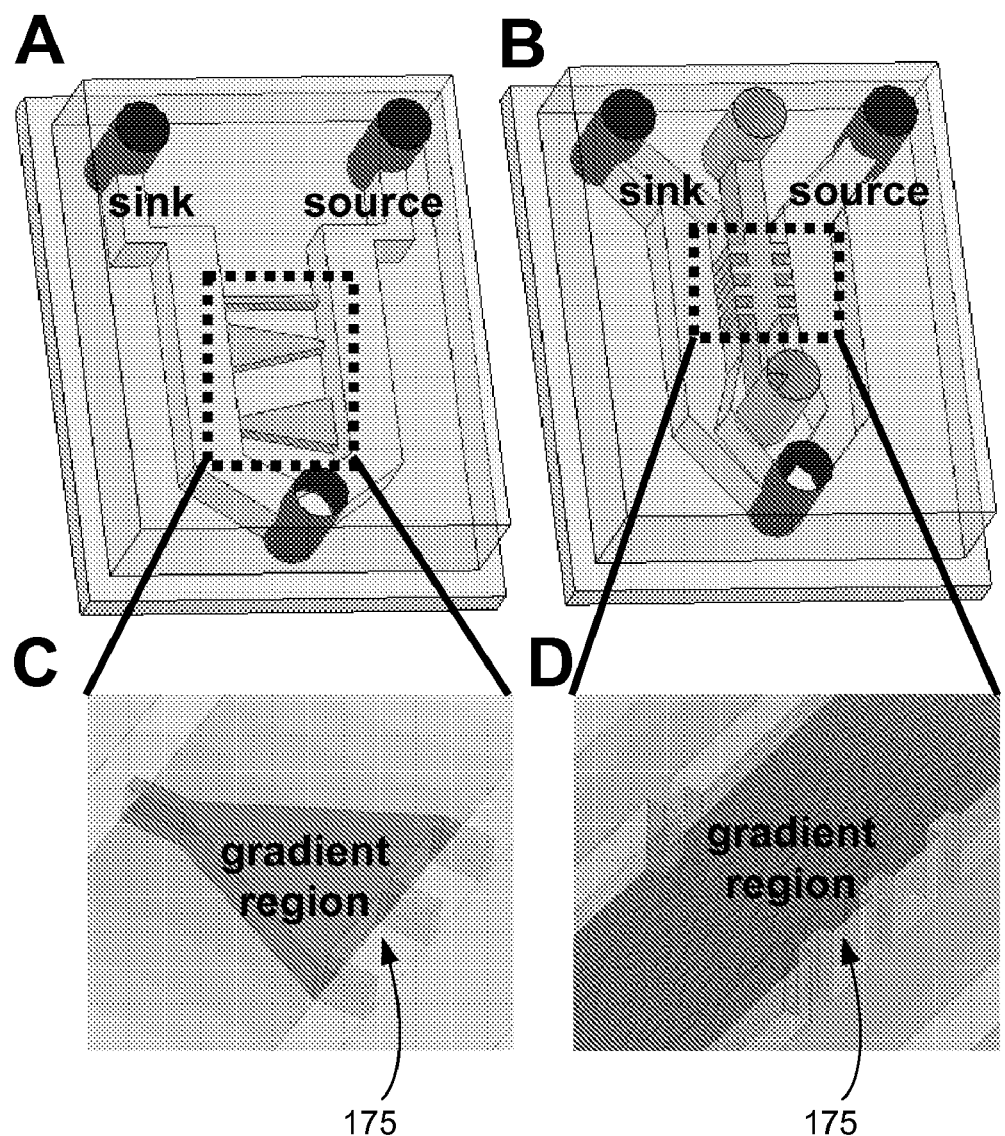
FIG. 3 panel A depicts an embodiment of a gradient device including exemplary gradient chambers suitable for generating gradients in two-dimensions.

Referring to FIG. 3 panel C, additional modifications include post structure 175 situated at or near the interface of a gradient chamber and main channels. Such structures may provide additional resistance when large opening are needed for non-linear gradient profiles.

Linear gradients may be generated when the interface conditions are such that the molecular flux area is constant across a gradient generating region, as in a straight channel (see e.g., FIG. 1, element 125). The generation of non-linear profiles useful for both chemical and biological conditions may be achieved by modifying the flux area associated with the gradient generating region. Referring to FIG. 1, modifying the geometric design of the gradient chamber and the relative openings to source and sink channels may be used to modulate a gradient profile. A symmetric gradient chamber (see e.g., element 125) may produce a linear gradient profile where the slope of the gradient is substantially dependent on the length of the gradient generating region.

Non-linear profiles may be produced by manufacturing a gradient chamber in an asymmetric configuration (see e.g., elements 130 and 135). This arrangement provides a continual imbalance of the in-flux and out-flux area between the source and sink channels through which molecules diffuse. The degree of non-linearity may also be changed by curved gradient chambers.

Gradient profiles may also be controlled by modifying the ratio of the number of sink to source openings (e.g., the area of the gradient generating region through which molecules diffuse). Linear gradients may be produced when the openings are symmetric and evenly distributed at opposite ends since the in-flux and out-flux area of the diffusing molecules are equal. Non-linear gradients may be produced when the number of openings are unbalanced causing an unequal in-flux and out-flux area in the gradient generating region. The degree of non-linearity can be enhanced by increasing the ratio of openings and shortening the width of the gradient generating region.

Further, gradient profiles may be controlled by modifying the concentrations of the source and sink constituents, which can be further controlled temporally by switching the inlet solutions.

Also encompassed by embodiments of gradient devices provided herein are complex gradient profiles made by a serial combination of a plurality of gradient chamber or gradient bridge designs within a gradient generating region. For example, juxtaposing a concave down and concave up non-linear profile will yield a sigmoidal gradient profile. For the gradient device shown in FIG. 1, this may be achieved by arranging the gradient chamber in a "bow-tie" shape with wide openings to the source and sink channels and tapering towards the middle of the chamber. For the gradient device shown in FIG. 2, a complex gradient profile may be achieved by configuring multiple gradient generating regions to include multiple apertures to the source and sink channels on the outer sides and fewer connecting apertures in the middle. Additionally, since various types of gradient device designs can be integrated during fabrication, a variety of both linear and non-linear profiles can be generated on a single device or platform for high-throughput experiments.

Figure 2:
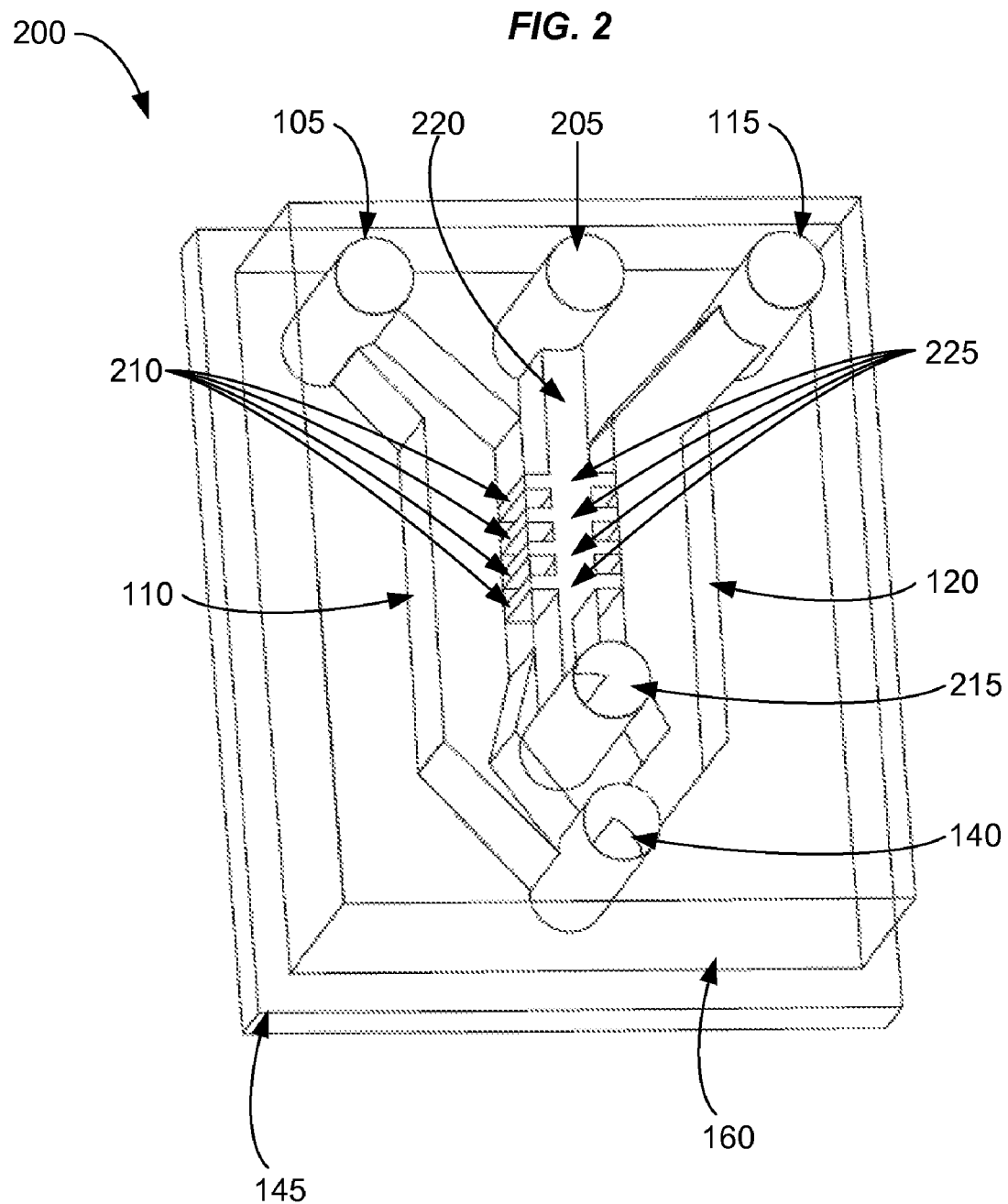
FIG. 2 depicts an embodiment of a gradient device including an exemplary bridge channel including a plurality of gradient bridges.

A second exemplary embodiment of a gradient generating device is depicted in FIG. 2. Gradient device 200 is configured to include gradient bridge 210 fluidly associated with sink channel 110 and source channel 120. It is understood that while FIG. 2 depicts multiple gradient bridges, a gradient device that includes a single gradient bridge is also encompassed by this embodiment. Gradient bridge 210 is configured to facilitate the formation of gradient generating region(s) 225. Gradient device optionally includes bridge channel 220 fluidly associated with gradient bridge 210. Bridge channel is a fluidly associated with bridge channel inlet 205.

Gradient generating device 200 may be configured to accommodate a matrix functionally associated with gradient bridge 210 and optionally bridge channel 220. In this embodiment, the formation of a gradient in a gradient generating region 225 occurs within the matrix. As the device generates gradients across a gradient generating region by free-diffusion between a source and a sink channel, convective flow through a gradient chamber may be minimized by selectively filling the gradient generating region with a 3D matrix (e.g., collagen gel) which increases the fluidic resistance minimizing flow penetration into the gradient generating region. Referring to FIG. 3 panel D, additional modifications include post structure 175 situated at or near the interface of a gradient bridge and main channels. Such structures may provide additional resistance when large opening are needed for non-linear gradient profiles.

Gradient generating device 200 including a matrix provides conditions suitable for studying cell motility and chemotaxis in the presence of a gradient containing a soluble factor. For example, a soluble factor may be present in the source constituent. The source constituent may be added to source channel 115. A cell may be added to the matrix associated with gradient bridge 210 or bridge channel 220. Sink channel 110 containing sink constituent (i.e. source constituent minus soluble factor). A gradient of soluble factor forms in bridge channel a gradient generating region 225. Cell activity in relation to the gradient can be determined by e.g., microscopy.

The generation of linear and non-linear gradients may be accomplished. Referring to FIG. 3 panels B and D, modifying the geometric design of the gradient bridge and the relative openings to source and sink channels may be used to modulate a gradient profile in a matrix. Gradient profiles may be controlled by modifying the ratio of the number of sink to source openings (e.g., the area of the gradient generating region through which molecules diffuse). Linear gradients may be produced when the openings are symmetric and evenly distributed at opposite ends since the in-flux and out-flux area of the diffusing molecules are equal. Non-linear gradients may be produced when the number of openings are unbalanced causing an unequal in-flux and out-flux area in the gradient generating region. The degree of non-linearity can be enhanced by increasing the ratio of openings and shortening the width of the gradient generating region.

Also encompassed by embodiments of gradient devices provided herein are complex gradient profiles made by a serial combination of a plurality of gradient chamber or gradient bridge designs within a gradient generating region. For the gradient device shown in FIG. 2, a complex gradient profile may be achieved by configuring multiple gradient generating regions to include multiple apertures to the source and sink channels on the outer sides and fewer connecting apertures in the middle. Additionally, since various types of gradient device designs can be integrated during fabrication, a variety of both linear and non-linear profiles can be generated on a single device or platform for high-throughput experiments. The following published applications are incorporated herein by reference in their entirety: U.S. Publication No. 20040106192, U.S. Publication No. 20040121066, and U.S. Publication No. 20050217750. The term "microfluidic" refers to a system or device for handling, processing, ejecting and/or analyzing a fluid sample including at least one channel having microscale dimensions. The terms "channel," "sink channel," or "source channel" as used herein refers to a pathway formed in or through a medium that allows for movement of fluids, such as liquids and gases. The channel in a device or system provided herein may include cross-sectional dimensions in the range between about 1.0 µm and about 500 µm, between about 25 µm and about 250 µm and between about 50 µm and about 150 µm. One of ordinary skill in the art will be able to determine an appropriate volume and length of the channels. The ranges are intended to include the above-recited values as upper or lower limits. A channel can have any selected shape or arrangement, examples of which include a linear or non-linear configuration and a U-shaped configuration.

Microfluidic gradients created in accordance with the devices and methods as described herein may be useful in a variety of applications. As specifically described in detail below, the flow-free diffusion that occurs at the gradient generating region (GGR) may provide conditions advantageous in the formation of crystals, as well as in the performance of certain assays for cell motility and chemotaxis.

Figure 4:
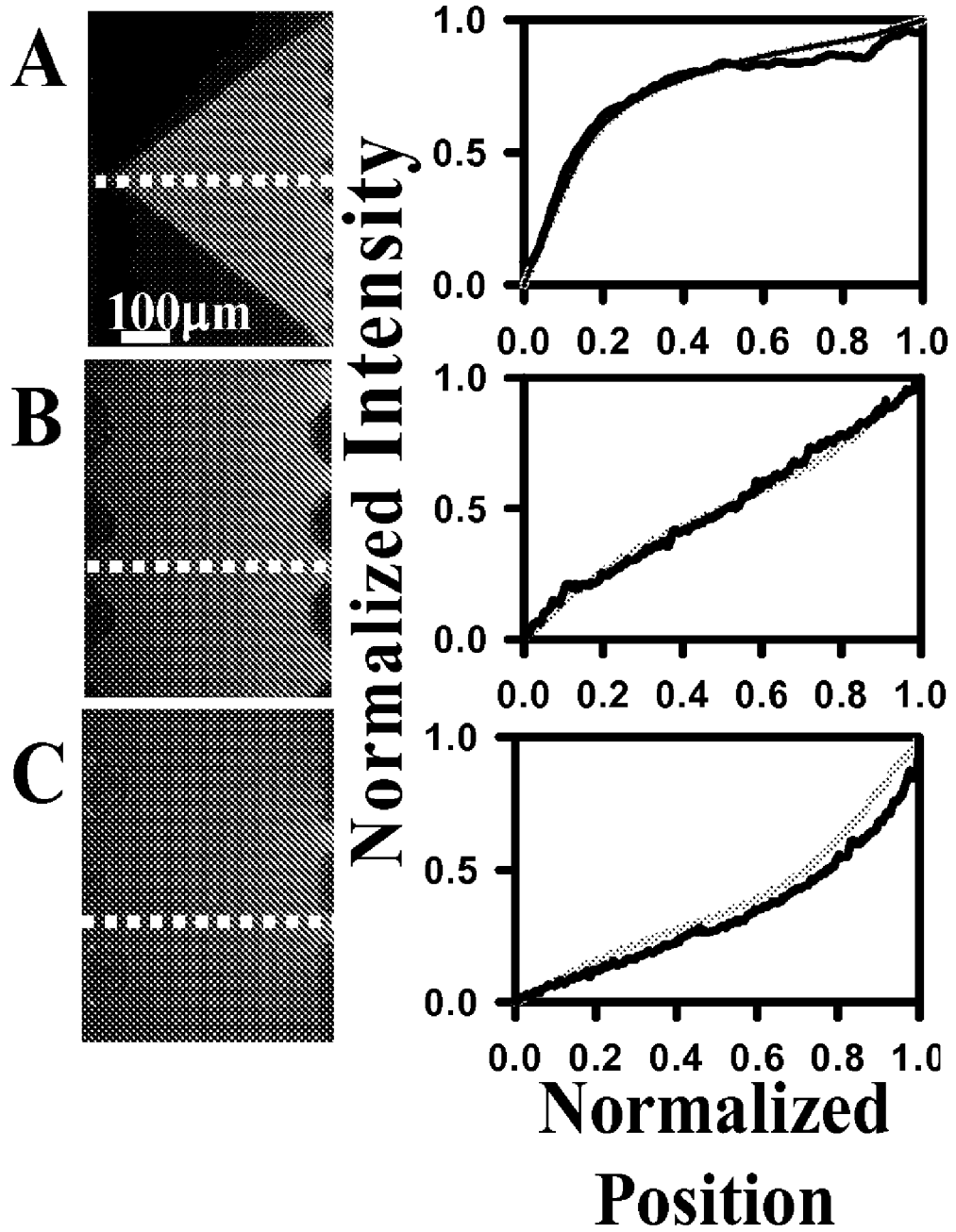
FIG. 4 panel A depicts an exemplary gradient profile (right panel) and fluorescent images (left panel) produced by a gradient device provided herein.
Figure 5:
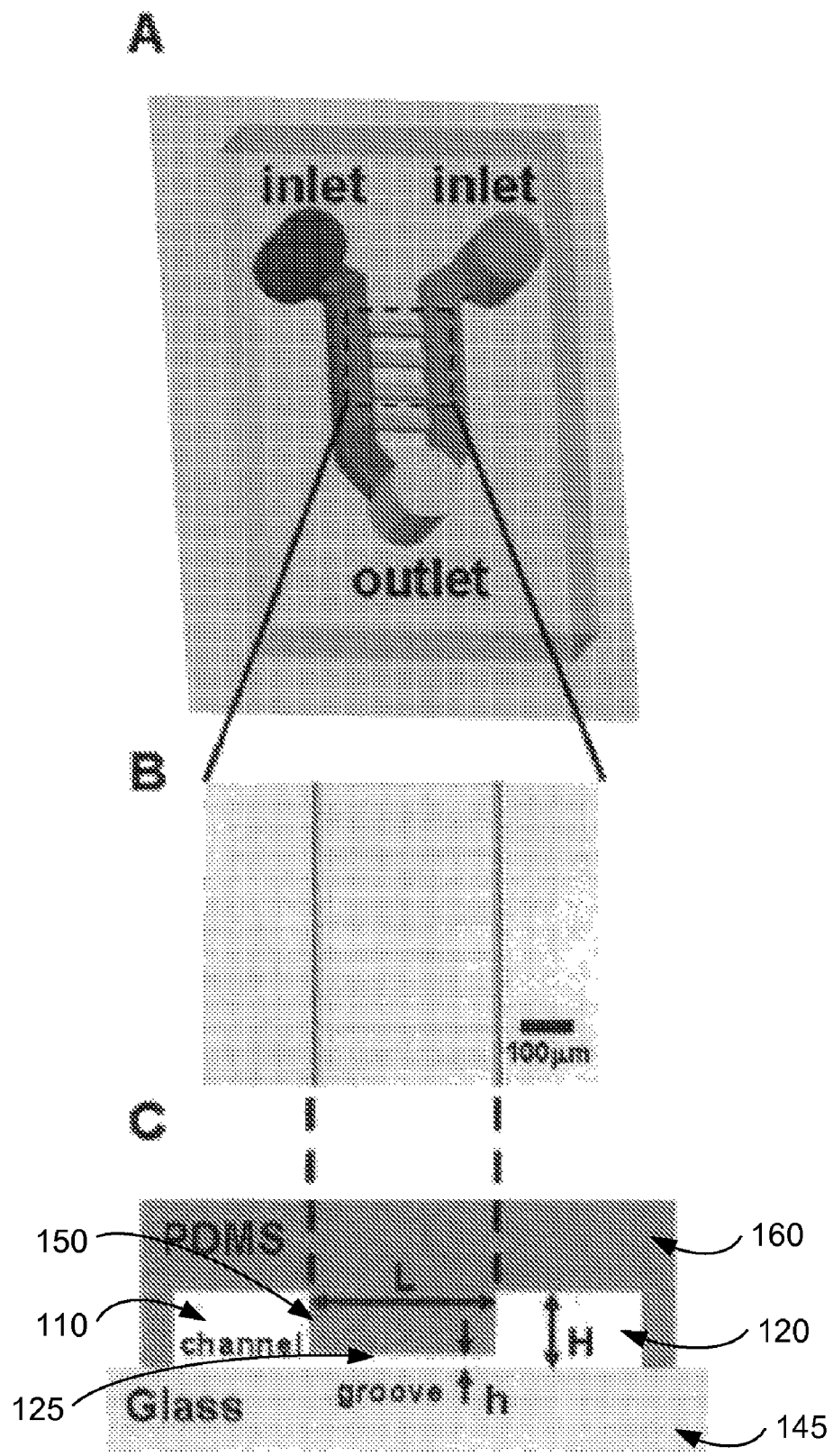
FIG. 5 panel A depicts an embodiment of a gradient device including a plurality of gradient chambers.
Figure 6:
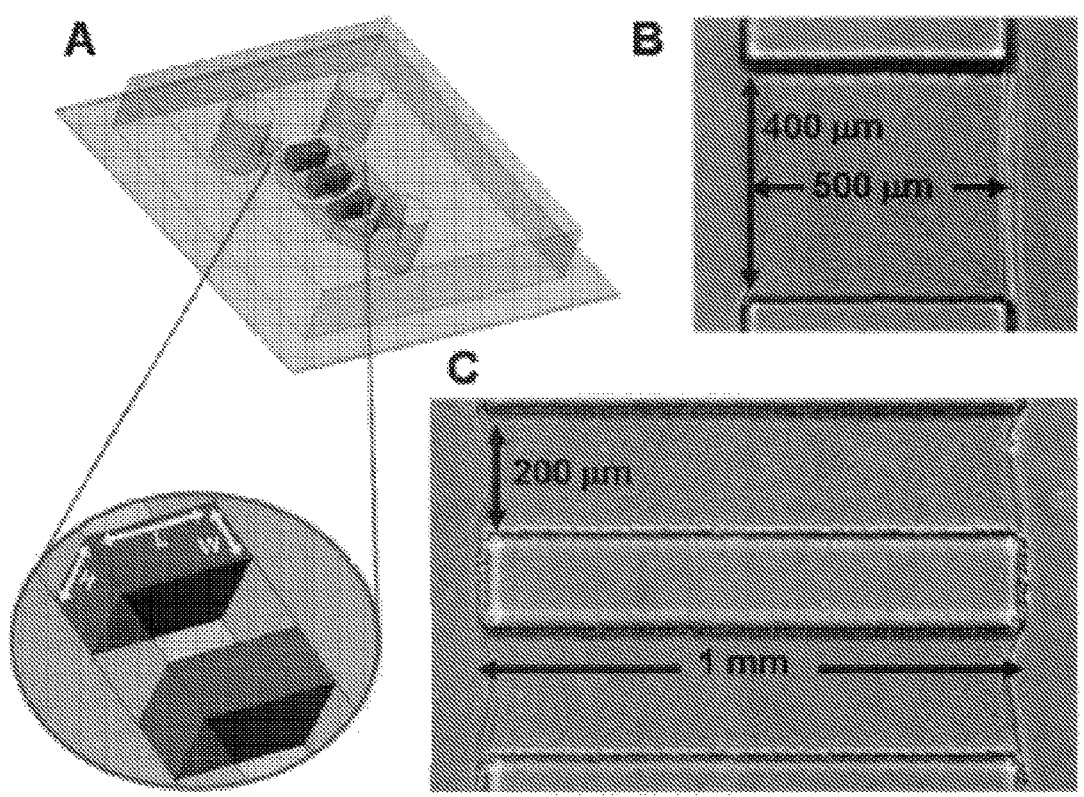
FIG. 6 panel A depicts an embodiment of a gradient device including a plurality of gradient bridges.

Provided herein are devices and methods suitable for facilitating free-diffusion between dynamically replenished flow channels acting as a sink and source to give rise to stable steady-state profiles. Such devices are particularly well-suited for forming 3D matrices for studying a molecular event associated with cell migration and/or the activity of a cell in a particular microenvironment. Referring again to FIG. 3 panel B, the gradient generating region in this embodiment includes a 3D matrix. FIG. 3 panel D depicts a gradient generating region for a 3D matrix with asymmetric posts designed to produce non-linear gradient. FIG. 4 depicts fluorescent images and corresponding experimental (black) and theoretical (grey) gradient profiles across GGR; intensity profiles taken across white dash line. FIG. 4 panel B depicts gradients across 3D matrigel produced using a design shown in FIG. 2 or FIG. 3, panel B. Linear profiles were produced by designing the same number of openings to source and sink channels. Referring to FIG. 4 panel C, mismatched number of openings to source and sink channels resulted in a non-linear profile. The openings were about 50 µm wide.

Devices and methods provided herein are suitable for studying live cells. For example, the devices can be used to successfully observe chemotaxis of a cell in a gradient of a soluble factor such as, for example, a chemokine. The device can be placed on a microscope during the experiment and time-lapse micrographs taken at various intervals. Computer controlled pumps can used to infuse agents such as media or chemokines into the device. For example, human cancer cells chemotax when exposed to gradients of a variety of growth factors. A gradient device provided herein can be used to examine the behavior of cells in a controlled fluidic microenvironment containing autocrine/paracrine factors for cell signaling investigations.

Referring again to FIG. 1, a gradient device provided herein can be used to produce crystalline structures of target molecules. Crystallization is an important technique to the biological and chemical arts. A high-quality crystal of a target molecule can be analyzed by x-ray diffraction techniques to produce an accurate three-dimensional structure of the target. This three-dimensional structure information can then be utilized to predict functionality and behavior of the target. Forming a high quality crystal is generally difficult. The gradient devices and methods provided herein are particularly suited to crystallizing biological macromolecules or complexes thereof, such as proteins, nucleic acids, viruses, and protein/ligand assemblies. However, devices and methods provided herein are not limited to any particular type of target material.

In general, protein crystallization may be accomplished utilizing a device provided herein. For example, referring to FIG. 1, a gradient can be formed by introducing a source constituent into a source channel, and introducing a sink constituent containing a countersolvent or crystallizing agent into sink channel. A gradient is formed at the gradient generating region in the gradient chamber, thereby allowing for formation of a diffusion gradient between the source constituent and the sink constituent containing the crystallizing agent. As a result of diffusive mixing between the sample and the crystallizing agent, the solution environment is gradually changed, resulting in the formation of protein crystals in the chamber.

Typical targets for crystallization are diverse. A target for crystallization may include but is not limited to: 1) biological macromolecules (cytosolic proteins, extracellular proteins, membrane proteins, DNA, RNA, and complex combinations thereof), 2) pre- and post-translationally modified biological molecules (including but not limited to, phosphorylated, sulfolated, glycosylated, ubiquitinated, etc. proteins, as well as halogenated, abasic, alkylated, etc. nucleic acids); 3) deliberately derivatized macromolecules, such as heavy-atom labeled DNAs, RNAs, and proteins (and complexes thereof), seleno methionine-labeled proteins and nucleic acids (and complexes thereof), halogenated DNAs, RNAs, and proteins (and complexes thereof), 4) whole viruses or large cellular particles (such as the ribosome, replisome, spliceosome, tubulin filaments, actin filaments, chromosomes, etc.), 5) small-molecule compounds such as drugs, lead compounds, ligands, salts, and organic or metallo-organic compounds, and 6) small-molecule/biological macromolecule complexes (e.g., drug/protein complexes, enzyme/substrate complexes, enzyme/product complexes, enzyme/regulator complexes, enzyme/inhibitor complexes, and combinations thereof). Such targets are the focus of study for a wide range of scientific disciplines encompassing biology, biochemistry, material sciences, pharmaceutics, chemistry, and physics.

During crystallization screening, a large number of chemical compounds may be employed. These compounds include salts, small and large molecular weight organic compounds, buffers, ligands, small-molecule agents, detergents, peptides, crosslinking agents, and derivatizing agents. Together, these chemicals can be used to vary the ionic strength, pH, solute concentration, and target concentration in the drop, and can even be used to modify the target. The desired concentration of these chemicals to achieve crystallization is variable, and can range from nanomolar to molar concentrations. A typical crystallization mix contains set of fixed, but empirically-determined, types and concentrations of 'precipitants', buffers, salts, and other chemical additives (e.g., metal ions, salts, small molecular chemical additives, cryo protectants, etc.). Water is a key solvent in many crystallization trials of biological targets, as many of these molecules may require hydration to stay active and folded.

Precipitating agents act to push targets from a soluble to insoluble state, and may work by volume exclusion, changing the dielectric constant of the solvent, charge shielding, and molecular crowding. Precipitating agents compatible with the PDMS material of certain embodiments of the device provided herein include, but are not limited to, salts, high molecular weight polymers, polar solvents, aqueous solutions, high molecular weight alcohols, and divalent metals.

Precipitating compounds, which include large and small molecular weight organics, as well as certain salts, are used from under 1% to upwards of 40% concentration, or from less than 0.5M to greater than 4M concentration. Water itself can act in a precipitating manner for samples that require a certain level of ionic strength to stay soluble. Many precipitants may also be mixed with one another to increase the chemical diversity of the crystallization screen. The gradient devices described herein are readily compatible with a broad range of such compounds. Moreover, many precipitating agents (such as long- and short-chain organics) are quite viscous at high concentrations, presenting a problem for most fluid handling devices, such as pipettes or robotic systems.

Solution pH can be varied by the inclusion of buffering agents; typical pH ranges for biological materials lie anywhere between values of 3.5-10.5 and the concentration of buffer, generally lies between 0.01 and 0.25 M. The gradient devices described in this document are readily compatible with a broad range of pH values, particularly those suited to biological targets.

A nonexclusive list of possible buffers is as follows: Na/K-Acetate; HEPES; Na-Cacodylate; Na/K-Citrate; Na/K-Succinate; Na/K-Phosphate; TRIS; TRIS-Maleate; Imidazole-Maleate; BisTrisPropane; CAPSO, CHAPS, MES, and imidizole.

Additives are small molecules that affect the solubility and/or activity behavior of the target molecule. Such compounds can speed crystallization screening or produce alternate crystal forms of the target. Additives can take nearly any conceivable form of chemical, but are typically mono and polyvalent salts (inorganic or organic), enzyme ligands (substrates, products, allosteric effectors), chemical crosslinking agents, detergents and/or lipids, heavy metals, organo-metallic compounds, trace amounts of precipitating agents, and small and large molecular weight organics.

In addition to chemical variability, a host of other parameters can be varied during crystallization screening. Such parameters include but are not limited to: 1) volume of crystallization trial, 2) ratio of target solution to crystallization solution, 3) target concentration, 4) cocrystallization of the target with a secondary small or macromolecule, 5) hydration, 6) incubation time, 7) temperature, 8) pressure, 9) contact surfaces, 10) modifications to target molecules, and 11) gravity.

Volumes of crystallization trials can be of any conceivable value, from the picoliter to milliliter range. Typical values may include but are not limited to: 0.1, 0.2, 0.25, 0.4, 0.5, 0.75, 1, 2, 4, 5, 10, 15, 20, 25, 30, 35, 40, 45, 50, 60, 70, 75, 80, 90, 100, 125, 150, 175, 200, 225, 250, 275, 300, 350, 400, 450, 500, 550, 600, 700, 750, 800, 900, 1000, 1100, 1200, 1250, 1300, 1400, 1500, 1600, 1700, 1800, 1900, 2000, 2250, 2500, 3000, 4000, 5000, 6000, 7000, 7500, 8000, 9000, and 10000 mL. The gradient devices previously described can access these values.

In particular, access to the low volume range for crystallization trials (<100 mL) is a distinct advantage of embodiments of the gradient devices provided herein. Small-volume gradient chambers for crystallization studies can be readily designed and fabricated, minimizing the need the need for large quantities of precious target molecules. The low consumption of target is particularly useful in attempting to crystallize scarce biological samples such as membrane proteins, protein/protein and protein/nucleic acid complexes, and small-molecule drug screening of lead libraries for binding to targets of interest.

Co-crystallization generally describes the crystallization of a target with a secondary factor that is a natural or non-natural binding partner. Such secondary factors can be small, on the order of about 10-1000 Da, or may be large macromolecules. Co-crystallization molecules can include but are not limited to small-molecule enzyme ligands (substrates, products, allosteric effectors, etc.), small-molecule drug leads, single-stranded or double-stranded DNAs or RNAs, complement proteins (such as a partner or target protein or subunit), monoclonal antibodies, and fusion-proteins (e.g., maltose binding proteins, glutathione S-transferase, protein-G, or other tags that can aid expression, solubility, and target behavior). As many of these compounds are either biological or of a reasonable molecular weight, co-crystallization molecules can be routinely included with screens in the gradient generating devices.

Gradient device designs may include nonreactive, biocompatible environments. Thus, the composition of the gradient chambers in the gradient device can be varied to provide new surfaces for forming e.g., crystallized molecules. In addition, the small size of the gradient chambers allows e.g., crystallization attempts under hundreds or even thousands of different sets of conditions to be performed simultaneously.

Exemplary Materials and Methods

Provided herein are monolithic microfluidics-based gradient generating devices that can generate an array of complex steady-state soluble molecular gradients in flow-free 2D and 3D environments. Three dimensional hydrogels are increasingly used in the investigation of many cell behaviors as they simulate in-vivo conditions better than 2D models. Investigations on invasive migration of metastatic cancer cells and stem cell niches can benefit greatly if complex, stable molecular gradients can be achieved across 3D gels in flow-free conditions. The design principles provided herein may be applied to build complex profiles by simply engineering the shape of the gradient generating region as set forth in various embodiments of devices described herein. Continuously replenished source and sink are advantageous over static reservoirs because their concentration can be kept constant and thus the gradients can be maintained at constant profile at steady-state.

Device Fabrication: A master was made by two rounds of photolithography on a silicone wafer. The first layer patterns the gradient chambers or gradient bridges and the second layer patterns the source or sink channels. The transparency masks were drawn in Freehand 9.0, and then printed by PAGE ONE DIGITAL (Irvine, Calif.). The silicone wafer (Silicon, Inc.-Boise, Id.) was plasma cleaned (Harrick Scientific Corp.-Ossining, N.Y.) for a suitable time period (e.g., 5 minutes) and then covered with SU-8 5 photoresist (Microchem, Inc.-Newton, Mass.) by spincastting at about 3,500 rpm for about 1 min to yield a thickness of 3.3 µm. The coated wafer was baked for 1 min at 100° C. in a leveled oven. The wafer was then exposed to UV light for 7 seconds at 25 mW/cm$^2$ and baked again for 1 min at 100° C. Finally, the wafer was placed into developer removing SU-8 from unexposed regions. The patterned wafer was then air-dried and a second layer was applied using SU-8 50; the thickness is a 100 µm by spincasting at 1,000 rpm for 1 minute. For aligning purposes, tape was used over the aligner marks so that the photoresist will not conceal them. The remaining features were then patterned with the same procedure as above except for baking and exposure time. After second layer coating, the wafer is baked for 30 min at 100° C. and exposed to UV for 20 seconds at 25 mW/cm$^2$. The wafer was baked again for 10 min at 100° C. and then developed. The finalized wafer was then silanized in a desiccator for 2 hours and then placed in a plastic petri dish and filled with PDMS. PDMS was made using a 10:1 ratio of prepolymer and catalyst. The PDMS was baked at 80° C. for 3 hours to become fully polymerized. The PDMS pattern is then cut from the master mold with inlet and outlet holes punched out. A glass slide and the prepared device were plasma cleaned for 2 minutes. The device and slide glass were then sealed irreversibly together with channels formed at the interface.

Additional methods for manufacture a device provided herein are known to the skilled artisan. For example, in soft lithographic bonding, elastomeric layers may be bonded together chemically, using chemistry that is intrinsic to the polymers comprising patterned elastomer layers. The bonding may include two component "addition cure" bonding. The various layers of elastomer may be bound together in a heterogeneous bonding in which the layers have a different chemistry. Alternatively, a homogenous bonding may be used in which all layers would be of the same chemistry. Thirdly, the respective elastomer layers may optionally be glued together by an adhesive. In a fourth aspect, the elastomeric layers may be thermoset elastomers bonded together by heating.

The elastomeric layers may be composed of the same elastomer material, with the same chemical entity in one layer reacting with the same chemical entity in the other layer to bond the layers together. Alternatively, bonding between polymer chains of like elastomer layers may result from activation of a crosslinking agent due to light, heat, or chemical reaction with a separate chemical species.

Further, the elastomeric layers may be composed of different elastomeric materials, with a first chemical entity in one layer reacting with a second chemical entity in another layer. Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", Analytical Chemistry (1998), 70, 4974-4984, incorporated herein by reference. This paper discloses that exposing polydimethyl-siloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Two different methods (depending on the device design) were used to selectively localize the gels in the gradient generating region. For devices with gradient bridge design (e.g., FIG. 2), the entire device was first filled with liquid gel followed by rapid aspiration with house vacuum. Since the resistance across the gradient generating region is considerably higher than across the main channels, the gel in the G gradient generating region were selectively left behind. The second method requires simple loading of liquid gel into the gradient generating region inlet and can be used with the design shown in FIG. 3 panel B. After plasma treatment and bonding, channel surfaces were allowed to revert back to a hydrophobic state before injecting the gel into gradient generating region. The gel was confined to the gradient generating region by surface tension until it solidified and then used for gradient experiments. A number of gel materials such as collagen type I, Matrigel, and fibrin were successfully polymerized in the device using both methods.

Gradient Characterization: The gradient profiles were generated and compared through an experimental fluorescent image of a chemical gradient and a simulated model. The experimental gradient was formed by a fluorescent molecule Fluorescein isothiocyanate (FITC), isomer I, 90% (Aldrich-Steinheim, Germany) which has a molecular weight of 389.39 g/mole. The solutions used were deionized water and 1% FITC solution in deionized water. After the flow began by pumping (Harvard Apparatus Picoplus-Woodstock, Conn.) at 2 µl/min from each outlet, the device was allowed to reach steady-state and bright-field and fluorescent pictures were taken. Centerline intensity profiles were taken and normalized. These profiles were compared to simulated centerline concentration profiles that were also normalized. The simulated profiles were generated by a finite element modeling software designated Comsol 3.2. The simulated gradient profile is based on a system with the exact geometry of the transparency mask with solely diffusion as a means of transport from one end to the other. Diffusion as the sole means of transport was confirmed by flowing fluorescent bead through the main channels and observing that no beads convectively entered the gradient chamber or gradient bridge. The concentrations used were 100% and 0% signifying the use of a buffer on one side. For both the experimental and simulation, only the steady-state gradient profiles were evaluated. To ensure that steady-state was reached in the experiment, extra time was given to establish the gradient than predicted by the equation:

$$t = \frac{x^2}{2D}$$

where t is the time for the molecule to diffuse a distance, x is the distance the molecule will diffuse, and D is the diffusion coefficient.

In one exemplary device, the distance to be diffused may be 400 µm and the diffusion coefficient may be that of the exemplary fluorescent molecule FITC which has a molecular weight of 389.39 g/mole. In order to calculate the diffusion coefficient, two equations may be implemented which approximate the linear size of the molecule and equates the diffusion coefficient. The first equation approximates the linear size:

$$a \approx MW^{\frac{1}{3}}$$

where, a is the linear molecule size, and MW is the molecular weight of a molecule.

The molecular weight of FITC is 389.39 g/mole. Accordingly, a single molecule is that divided by Avogadro's number, $6.022 \times 10^{23}$ molecules/mole, which yields $6.466 \times 10^{-22}$ g/molecule. Therefore a is equal to $8.65 \times 10^{-8}$ cm. The equation for the diffusion coefficient is:

$$D = \frac{kT}{6\pi\eta a}$$

where, k is the Boltzmann constant, T is the temperature, $\eta$ is the fluid viscosity, and a is the linear molecule size. The values for T, $\eta$, and a, are 300° K, 0.01 g/cm/s, $8.65 \times 10^{-8}$ cm, respectively; this calculates a value for D of $2.54 \times 10^{-6}$ cm$^2$/s. Utilizing this value for D approximates the steady-state time to be about 5.24 minutes.

The experimental data for intensity values may include data processing due to shadowing effects from the fluorescence signal in the main channels. In some embodiments, the main channels (e.g., source, sink and/or bridge channels) may be about 2 to 100 times the height of the side channels (e.g., gradient chamber or gradient bridge) which may result in a shadowing effect. This effect may be compensated for by subtracting an intensity linescan at a location where there is no side channel (e.g., gradient chamber or gradient bridge) from the linescan taken at the desired side channel. Accordingly, the first part of the data processing may follow the equation $$I_f = I_{sc} - I_{ref}$$

where $I_f$ is the plotted intensity value, $I_{sc}$ is the intensity value taken at the side channel, and $I_{ref}$ is the intensity value taken at a reference location. This removes both the ambient signal from the main channels and background noise from the signal originating in the side channel.

The second part of the data processing may include normalizing both the intensity values and the positions along the channel so that the experimental and theoretical graphs align. The normalization subtracts the minimum intensity value within the line profile from each intensity value and then divides each value by the difference between the maximum and minimum intensity values. The normalization equation is written as:

$$\sum_{x=0}^{L} I(x)_{norm} = \frac{I(x) - I_{min}}{I_{max} - I_{min}}$$

where $I(x)_{norm}$ is the normalized intensity value for a given pixel, $I(x)$ is the intensity value calculated from the above equation for a given pixel, $I_{min}$ is the minimum intensity value of the linescan, $I_{max}$ is the maximum intensity value of the linescan, and L is the number of pixels in the linescan.

Figure 7:
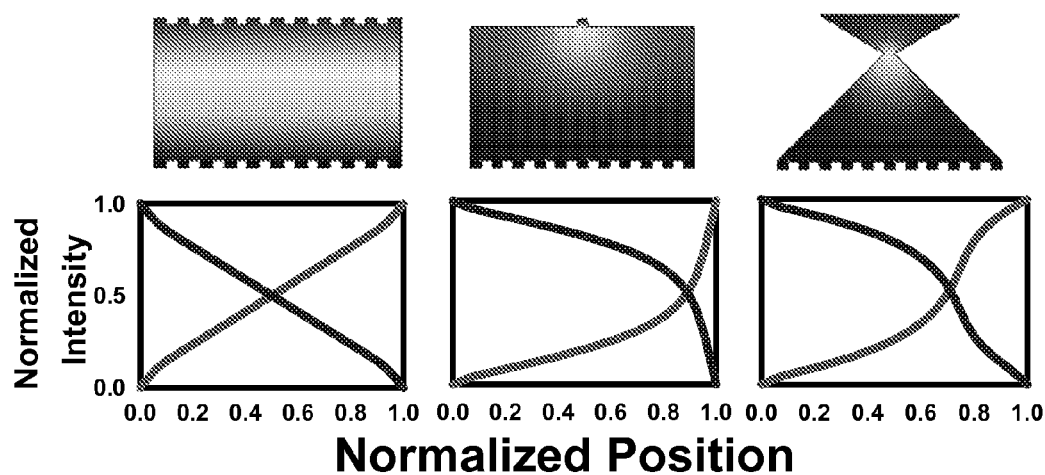
FIG. 7 depicts gradient profiles of three exemplary gradient chambers.

Referring to FIG. 7, profiles of three exemplary gradient chambers with their corresponding centerline gradient profile from both directions are provided. The left chamber yields a linear gradient, the middle chamber yields a non-linear gradient, and the right chamber is a juxtaposition of a concave-down and concave up non-linear gradient yielding an overall sigmoidal gradient profile.

Figure 8:
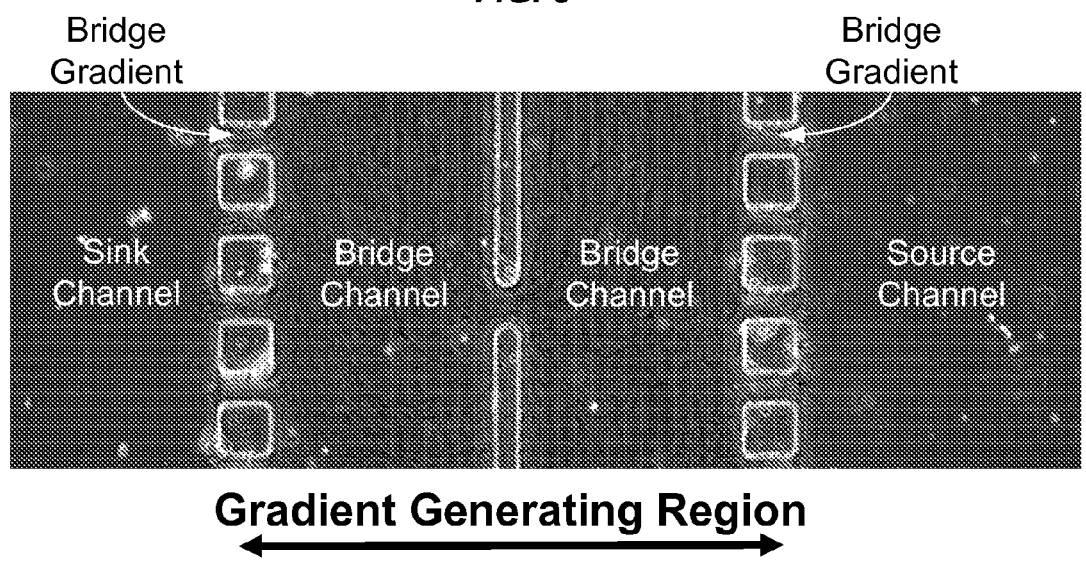
FIG. 8 depicts a collagen gel micrograph of an embodiment of a gradient device.

Collagen Gel Micrograph: Referring to FIG. 8, a micrograph of a collagen gel selectively polymerized in the gradient generating region of a gradient device is provided. In this embodiment, two juxtaposed bridge channels are shown in the gradient generating region. Gradient bridges appear as apertures between the "squares" flanking the bridge channels. In this embodiment, the gradient bridges provide fluid access from the source and sink channels to the bridge channel(s).

Figure 9:
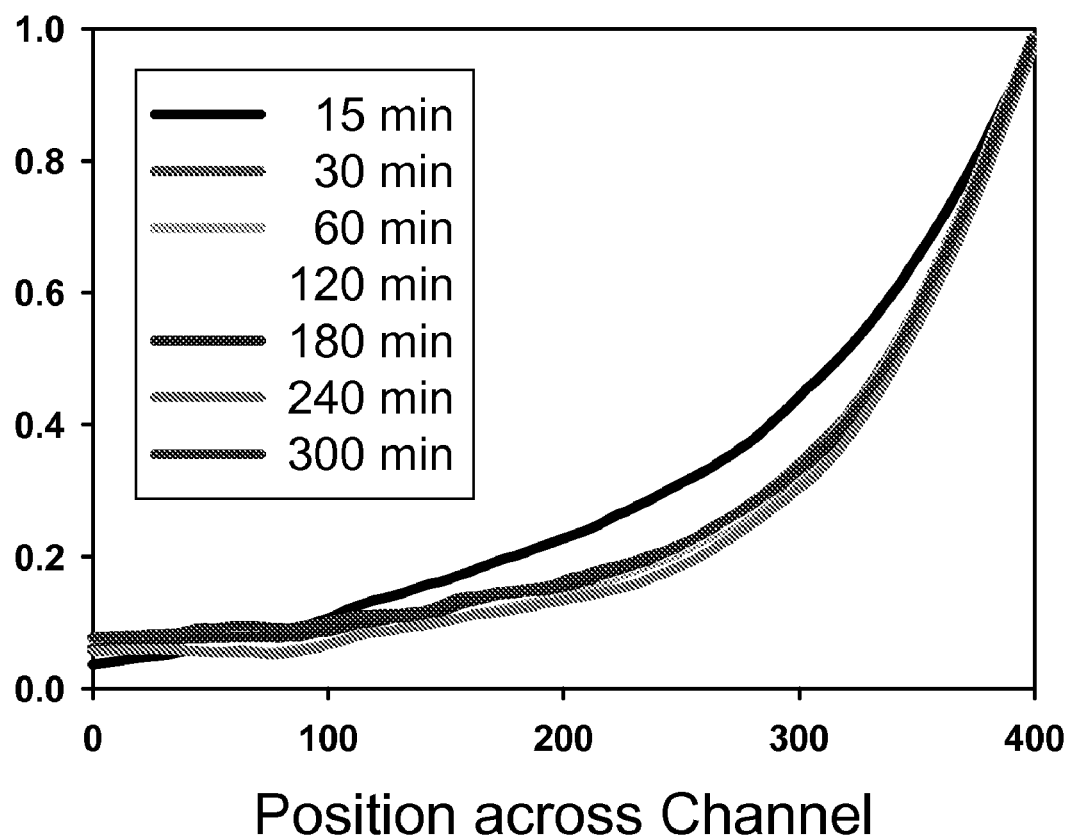
FIG. 9 depicts a graph of an exemplary concentration profile of a non-linear gradient across a collagen type 1 gel.

Gradient Stability over Time: A gradient device provided herein is suitable for maintaining a stable gradient over time. Such stability may depend upon the continual flow of source constituent and/or sink constituent through the main channels (e.g., the source, sink and/or bridge channels) of the device. Therefore after the steady-state gradient profile is reached, the profile will remain constant in the absence of flow disruption. FIG. 9 provides a graph of an exemplary concentration profile, taken over several time points, of a non-linear gradient across a collagen type 1 gel.

The examples set forth above are provided to give those of ordinary skill in the art a complete disclosure and description of how to make and use the embodiments of the device, systems and methods described herein, and are not intended to limit the scope of the various embodiments thereof. Modifications of the above-described modes for carrying out the device, systems and methods that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of devices, systems and methods have been described. Nevertheless, it will be understood that various modifications may be made without departing from the spirit and scope of such embodiments. Accordingly, other embodiments are within the scope of the following claims.

What is claimed is:

1. A gradient device comprising:
   a) a source channel in fluid communication with a first inlet;
   b) a sink channel in fluid communication with a second inlet and substantially parallel to the source channel;
   c) at least one gradient chamber disposed in proximity to the source channel and sink channel, the gradient chamber comprising at least a first terminal end in fluid communication with the source channel and at least a second terminal end in fluid communication with the sink channel,
   wherein the gradient chamber is configured to facilitate the formation of a gradient generating region substantially exclusively by diffusion.

2. The device of claim 1, wherein the gradient chamber is a microgroove.

3. The device of claim 1, wherein the height of the first and second terminal ends are less than the height of the source channel and sink channel.

4. The device of claim 1, further comprising a sensor for detecting a molecular event associated with the gradient chamber.

5. The device of claim 4, wherein the molecular event comprises formation of crystalline forms of a target molecule.

6. The device of claim 1, wherein the device is comprised of polydimethyl siloxane (PDMS).

7. The device of claim 1, wherein the gradient chamber is symmetrically configured to form a linear gradient.

8. The device of claim 1, wherein the gradient chamber is asymmetrically configured to form a non-linear gradient.

9. The device of claim 1 further comprising a plurality of gradient chambers.

10. The device of claim 1, wherein a stable gradient of soluble molecules is formed in a gradient generating region within a gradient chamber.

11. A gradient device comprising:
   a) a source channel in fluid communication with a first inlet;
   b) a sink channel in fluid communication with a second inlet and substantially parallel to the source channel;
   c) at least one gradient bridge disposed in proximity to the source channel and sink channel, the gradient bridge optionally in fluid communication with a bridge channel and comprising at least a first aperture in fluid communication with the source channel and at least a second aperture in fluid communication with the sink channel,
   wherein the gradient bridge and the gradient channel are configured to i) facilitate the formation of a gradient generating region substantially exclusively by diffusion and ii) contain a matrix suitable for sustaining cell migration.

12. The device of claim 11, wherein the matrix is a gel.

13. The device of claim 12, wherein the gel is a collagen type I gel.

14. The device of claim 11, further comprising a plurality of gradient bridges.

15. The device of claim 11, wherein the height of the first and second terminal apertures are substantially the same as the height of the source channel and sink channel.

16. The device of claim 11, further comprising a sensor for detecting a molecular event associated with the gradient bridge and gradient channel, or gradient bridge or gradient channel.

17. The device of claim 16, wherein the molecular event comprises chemotaxis associated with cell migration.

18. The device of claim 11 further comprising a plurality of gradient channels.

19. The device of claim 1, wherein a stable gradient of soluble molecules is formed in a gradient generating region within a gradient bridge or gradient channel, or gradient bridge and gradient channel.

20. A platform comprising a plurality of devices according to claims 1 or 11.

21. A system comprising: a) a device according to claim 1 or 11; b) a controller operably associated with the device according to claim 1 or 11, wherein the controller is configured to control fluid movement through the channels during operation of the device and c) a detector assembly configured to capture a molecular event associated with a gradient generation region.

22. The system of claim 21, wherein the detector assembly comprises an image acquisition device configured to synchronize the rate of image acquisition with gradient formation in the gradient generating region.

23. The system of claim 22, wherein the image acquisition device comprises a microscope.

24. A method of generating a gradient comprising:
   a) introducing a source constituent into the source channel of a device according to claim 1 or claim 11;
   b) introducing a sink constituent into the sink channel of a device of claim 1 or claim 11;
   c) providing a constant flow of source constituent and sink constituent;
   d) generating a gradient in the gradient chamber of claim 1 or the gradient bridge of claim 11, wherein the gradient comprises a substantially constant gradient profile.

25. The method of claim 24, wherein the source constituent comprises a soluble factor.

* * * * *